United States Patent
Reichow et al.

(10) Patent No.: US 8,240,851 B2
(45) Date of Patent: Aug. 14, 2012

(54) UNITARY VISION TESTING CENTER

(75) Inventors: Alan W. Reichow, Beaverton, OR (US); Ryan C. Coulter, Portland, OR (US)

(73) Assignee: Nike, Inc., Beaverton, OR (US)

(*) Notice: Subject to any disclaimer, the term of this patent is extended or adjusted under 35 U.S.C. 154(b) by 153 days.

(21) Appl. No.: 12/595,207

(22) PCT Filed: Apr. 14, 2008

(86) PCT No.: PCT/US2008/060229
§ 371 (c)(1),
(2), (4) Date: Mar. 23, 2010

(87) PCT Pub. No.: WO2008/128192
PCT Pub. Date: Oct. 23, 2008

(65) Prior Publication Data
US 2010/0188637 A1 Jul. 29, 2010

Related U.S. Application Data

(60) Provisional application No. 60/923,434, filed on Apr. 13, 2007, provisional application No. 60/941,915, filed on Jun. 4, 2007.

(51) Int. Cl.
*A61B 3/00* (2006.01)
(52) U.S. Cl. .......... 351/203; 351/239; 351/246
(58) Field of Classification Search ............. 351/203, 351/222, 223, 237, 239, 242, 243, 246
See application file for complete search history.

(56) References Cited

U.S. PATENT DOCUMENTS

| | | |
|---|---|---|
| 3,861,790 A | 1/1975 | Tamura |
| 4,528,989 A | 7/1985 | Weinblatt |
| 5,050,982 A | 9/1991 | Meissner |
| 5,088,810 A | 2/1992 | Galanter |
| 5,478,239 A | 12/1995 | Fuerst |
| 5,812,239 A | 9/1998 | Eger |
| 5,825,460 A | 10/1998 | Kohayakawa |
| 5,919,149 A | 7/1999 | Allum |

(Continued)

FOREIGN PATENT DOCUMENTS

WO 0017615 A2 3/2000

(Continued)

OTHER PUBLICATIONS

Office Action Mailed Apr. 6, 2011 in U.S. Appl. No. 12/595,209, 16 pages.

(Continued)

*Primary Examiner* — Huy K Mai
(74) *Attorney, Agent, or Firm* — Shook, Hardy Bacon L.L.P.

(57) ABSTRACT

System and methods for testing and/or training a subject's visual ability are provided. More specifically, the method may include testing various aspects of the subject's visual acuity, such as clarity, contrast, tracking, etc. By using various tests, a more efficient examination may be administered. In accordance with the invention, an individual may be tested using methods of testing and/or training at a unitary center, where the unitary center is capable of presenting visual tests to the individual, receiving input from the individual, and processing the received input. Such a unitary test center may further be configurable, so that the tests administered may vary based on the needs of the individual. The received input may then, for example, be used to compute data related to the user's visual acuity, both overall and for each individual test.

21 Claims, 4 Drawing Sheets

U.S. PATENT DOCUMENTS

| | | | |
|---|---|---|---|
| 6,092,058 | A | 7/2000 | Smyth |
| 6,261,239 | B1 | 7/2001 | Abraham-fuchs |
| 6,267,733 | B1 | 7/2001 | Peterson et al. |
| 6,364,845 | B1 | 4/2002 | Duffy et al. |
| 6,371,931 | B1 | 4/2002 | Guillen |
| 6,632,174 | B1 | 10/2003 | Breznitz |
| 6,755,525 | B2 | 6/2004 | Reichow |
| 6,811,258 | B1 | 11/2004 | Grant |
| 6,893,127 | B2 | 5/2005 | Reichow |
| 7,073,208 | B2 | 7/2006 | Penque |
| 7,326,060 | B2 | 2/2008 | Seiller et al. |
| 7,849,115 | B2 | 12/2010 | Reiner |
| 2003/0120183 | A1 | 6/2003 | Simmons |
| 2003/0211449 | A1 | 11/2003 | Seiller et al. |
| 2004/0141152 | A1 | 7/2004 | Marino et al. |
| 2005/0053904 | A1 | 3/2005 | Shephard |
| 2005/0273017 | A1 | 12/2005 | Gordon |
| 2006/0195018 | A1 | 8/2006 | Guillen |
| 2006/0244915 | A1 | 11/2006 | Clemons et al. |
| 2006/0251334 | A1 | 11/2006 | Oba et al. |
| 2006/0287617 | A1 | 12/2006 | Taub |
| 2007/0000007 | A1 | 1/2007 | MacDonald |
| 2007/0013870 | A1 | 1/2007 | Hara et al. |
| 2007/0052674 | A1 | 3/2007 | Culver |
| 2007/0254270 | A1 | 11/2007 | Hersh |
| 2008/0003553 | A1 | 1/2008 | Stark et al. |
| 2008/0189173 | A1* | 8/2008 | Bakar et al. .................. 705/14 |
| 2009/0093305 | A1 | 4/2009 | Okamoto et al. |
| 2009/0129205 | A1 | 5/2009 | Reichow |
| 2009/0130640 | A1 | 5/2009 | Hardy |
| 2009/0150919 | A1 | 6/2009 | Lee |

FOREIGN PATENT DOCUMENTS

| | | | |
|---|---|---|---|
| WO | 2004006747 | | 1/2004 |
| WO | 2006088415 | | 8/2006 |
| WO | 2007009990 | A1 | 1/2007 |
| WO | 2008128192 | | 10/2008 |

OTHER PUBLICATIONS

Office Action of Jan. 6, 2011 in U.S. Appl. No. 12/117,315, 16 pages.

Final Office Action of May 26, 2011 in U.S. Appl. No. 12/117,315, 10 pages.

International Search Report and Written Opinion for PCT/US08/60229, Mailed Sep. 9, 2008, 9 Pages.

Supplementary European Search Report for EP08745763, Completed Jun. 16, 2010, 9 Pages.

Rouse, et al., "A Comparison Study of Dynamic Visual Acuity Between Athletes and Nonathletes", Journal of the American Optometric Association, Dec. 1988, pp. 946-950, vol. 59, No. 12, United States.

Coffey, et al., "Optometric Evaluation of the Elite Athlete," Problems in Optometry, Mar. 1990, pp. 32-59, vol. 2, No. 1, United States.

Reichow, et al., "Introduction to Behavioral Optometry", Sports Vision, 1993, 75 pages, Optometric Extension Program Foundation, United States.

Reichow, et al., "A Comparison of Contrast Sensitivity in Elite Athletes Versus a Normal Population", American Journal of Optometry and Physiological Optics, Dec. 15, 1986, vol. 63, No. 82, United States.

Farrow, et al., "An Investigation of the Effectiveness of Bolle's Competivision Sport-Glasses on Tennis Performance", Clinical and Experimental Optometry, Jul.-Aug. 2000, pp. 226-231, vol. 83, No. 4.

Herdman, et al., "Computerized Dynamic Visual Acuity Test in the Assessment of Vestibular Deficits", The American Journal of Otology, 1998, pp. 790-796, vol. 19, No. 6, United States.

Tian, et al., "Dynamic Visual Acuity During Transient and Sinusoidal Yaw Rotation in Normal Ulilaterally Vestibulopathic Humans", Experimental Brain Research, Feb. 8, 2001, pp. 12-25, vol. 137, Springer-Verlag, United States.

"Coffey, et al., "Visual Performance Enhancement in Sports Optometry", Sports Vision 1995, pp. 158-177, Butterworth-Heinermann, United States."

Ferreira, "An Overview of Research in Sports Vision: its History and an Optometric Perspective", The South African Optometrist, Dec. 2003, pp. 142-149, vol. 62, No. 4, Auckland Park, South Africa.

Koenig, "Practicing Perception: Eyes Can Be Trained to be More Effective", USA Today Baseball Weekly, 1996, 3 pages, United States.

International Search Report and Written Opinion for PCT/US08/60249, Mailed Sep. 8, 2008, 9 Pages.

Supplementary European Search Report for EP08745783, Completed Jun. 23, 2010, 10 Pages.

International Search Report and Written Opinion for PCT/US08/60244, Mailed Sep. 4, 2008, 9 Pages.

Supplementary European Search Report for EP08745778.4, Completed Jun. 23, 2010, 9 Pages.

Supplementary European Search Report for EP08780526, Completed Jun. 16, 2010, 11 Pages.

International Search Report and Written Opinion for PCT/US08/60252, Mailed Aug. 15, 2008, 10 Pages.

International Search Report and Written Opinion for PCT/US09/043127, Mailed Jul. 6, 2009, 11 Pages.

Cardall, "Contact Lenses in Sport: a General Overview", Optician, Jan. 13, 2006, pp. 22-25, vol. 231, No. 6034, United States.

Reichow, et al., "Ultraviolet and Short Wavelength Visible Light Exposure: Why Ultraviolet Protection Alone is Not Adequate", Journal of Long-Term Effects of Medical Implants, 2006, pp. 315-325, vol. 16, No. 4, Begell House, Inc., United States.

Office Action of Jul. 12, 2011 in U.S. Appl. No. 12/595,209.

International Search Report and Written Opinion for PCT/US2010/041564, Mailed Nov. 12, 2010.

Office Action in U.S. Appl. No. 12/595,208 mailed Nov. 28, 2011, 20 pages.

Final Office Action in U.S. Appl. No. 12/595,209 mailed Jan. 13, 2012, 17 pages.

Non-Final Office Action in U.S. Appl. No. 12/500,385 mailed Mar. 19, 2012, 39 pages.

\* cited by examiner

UNITARY VISION TESTING CENTER

CROSS-REFERENCE TO RELATED APPLICATIONS

This application claims priority to U.S. Provisional Application No. 60/923,434 filed on Apr. 13, 2007, entitled "System and Method for Testing Visual Ability During Simulated Activity," which is hereby incorporated by reference. This application also claims priority to U.S. Provisional Application No. 60/941,915 filed on Jun. 4, 2007, entitled "System and Method for Decoupled Visual Ability Testing," which is hereby incorporated by reference.

STATEMENT REGARDING FEDERALLY SPONSORED RESEARCH OR DEVELOPMENT

Not applicable.

TECHNICAL FIELD

The present invention relates generally to the evaluation and/or training of an individual's visual abilities.

BACKGROUND OF THE INVENTION

Along with physical ability, an individual's sight plays a role in the individual's performance when participating in an activity, such as a sport. Typically, to improve in the sport or activity, an individual will focus on improving their physical ability to elevate their overall performance. By testing and training the individual's visual ability, however, the individual's performance may also improve.

SUMMARY OF THE INVENTION

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

In accordance with the invention, a method of testing and/or training a subject's visual ability is provided. More specifically, the method may include testing various aspects of the subject's visual ability, such as clarity, contrast, tracking, etc. By using various tests, a more streamlined examination may be administered. In accordance with the invention, an individual may be subjected to such a method of testing and/or training at a unitary center capable of presenting visual tests to the individual, receiving input from the individual, and processing the received input. Such a unitary test center may further be configurable, so that the tests administered may vary based on the needs of the individual. The received input may then, for example, be used to compute data related to the user's visual ability, both overall and for each individual test.

BRIEF DESCRIPTION OF THE DRAWING

The present invention is described in detail below with reference to the attached drawing figures, wherein.

DETAILED DESCRIPTION OF THE INVENTION

The subject matter of the present invention is described with specificity herein to meet statutory requirements. However, the description itself is not intended to limit the scope of this patent. Rather, the inventors have contemplated that the claimed subject matter might also be embodied in other ways, to include different steps or combinations of steps similar to the ones described in this document, in conjunction with other present or future technologies.

In accordance with the present invention, systems and methods for testing a subject's visual ability at a unitary testing unit are provided. Such a method may include testing various aspects of the subject's visual acuity, such as clarity, contrast, tracking, etc. at a unitary testing unit that may also be capable of processing the resulting data and/or transmitting data over a network to another location for processing. In doing so, the unitary testing center may streamline the process of testing the visual ability of subject, and may reduce overhead (e.g., reduce the equipment) needed to perform testing. Additionally, the unitary testing center may be configurable, so that the tests administered may vary based on the needs of the individual. The received input may then, for example, be used to compute results related to the user's visual ability, both overall and for each individual test.

In one embodiment, a testing device for testing the visual ability of a subject is provided. Such a testing device may include a presenting component, an input component, and a processing component, where the presenting component is capable of presenting a visual clarity test, a contrast sensitivity test, a visual tracking test, a distance focusing test, and a visual aiming test to the subject. In response to each test, the subject may provide input to the testing device. The input component may then be configured to receive the input, and the processing component may be configured to process the received input.

In another embodiment, a method for testing the visual ability of a subject, where the method occurs at a unitary location, is provided. The method comprises, in part, administering two or more vision ability tests to the test subject; receiving input from the test subject in response to each test; and processing the input received from the test subject.

Figure 1:
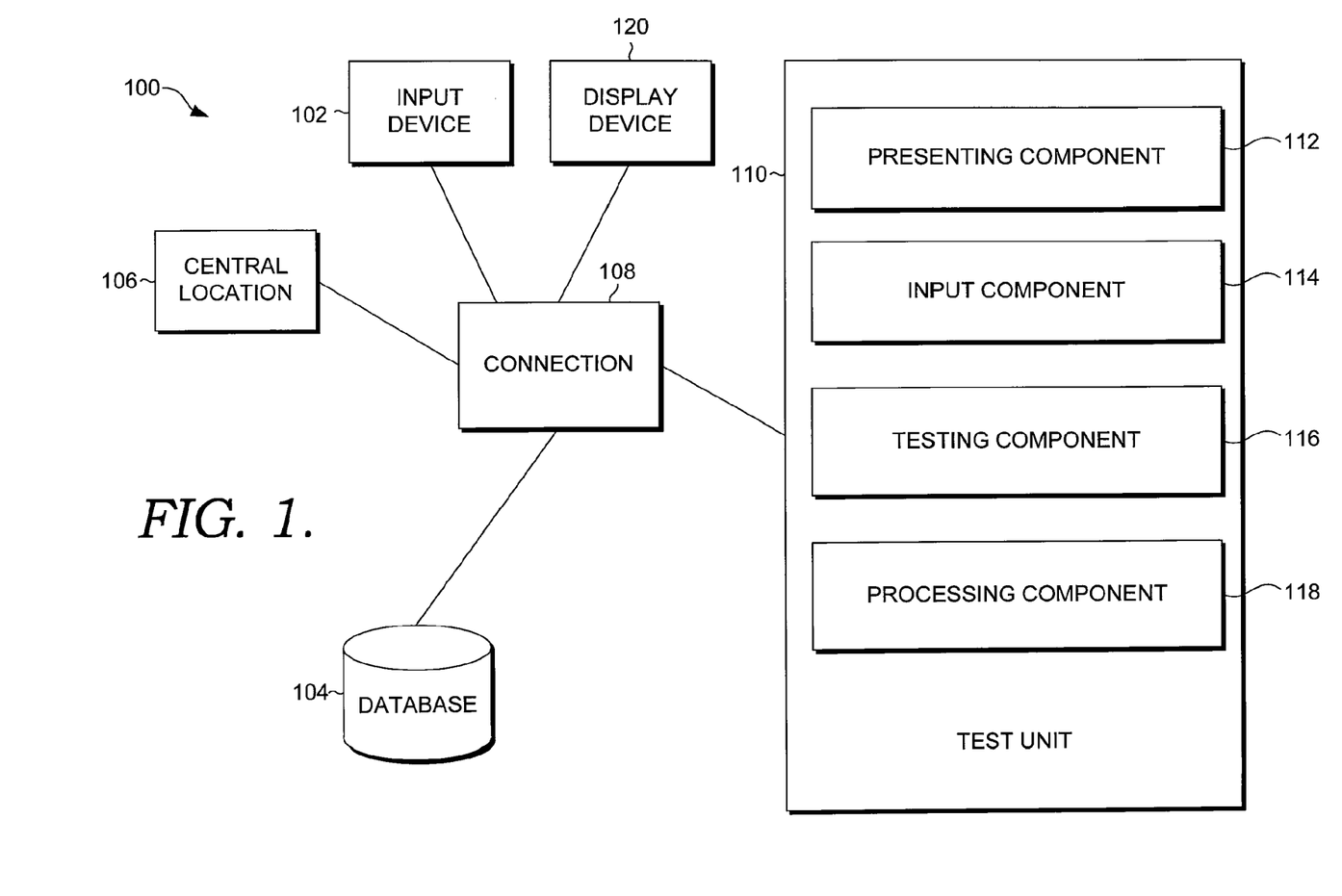
FIG. 1 is a block diagram of a computing system environment suitable for use in implementing the present invention.

Referring to the drawings in general, and initially to FIG. 1 in particular, a block diagram of an exemplary computing system is shown and designated generally as computing system 100 configured to provide for testing the visual ability of a subject. It will be understood and appreciated by those of ordinary skill in the art that the computing system 100 shown in FIG. 1 is merely an example of one suitable computing system environment and is not intended to suggest any limitation as to the scope of use or functionality of embodiments of the present invention. Neither should the computing system 100 be interpreted as having any dependency or requirement to any single component or combination of components illustrated therein.

The computing system 100 includes an input device 102, a display device 120, a database 104, a central location 106, and a test unit 110, all in communication with one another via a connection 108. The connection 108 may be made by wire (such as a cable), or wireless (such as a wireless network). Connection 108 may also be a network, where the network may include, without limitation, one or more local area networks (LANs) and/or wide area networks (WANs). Such networking environments are commonplace in enterprise-wide computer networks, intranets, and the Internet. Further, the connection 108 may comprise a locally wired connection between components of computing system 100. Accordingly, the connection 108 is not further described herein.

The input device 102 is capable of receiving one or more responses from a subject. Input device 102 may be any device that may receive responses from a subject. One skilled in the art will appreciate that more than one input device, such as input device 102, may be used with computing system 100. Input device 102 may be, for example, a microphone, joystick, game pad, wireless device, keyboard, keypad, game controller, treadmill, force plate, eye tracking system, gesture recognition system, touch sensitive screen, and/or any other input-initiating component that provides wired or wireless data to the test unit 110, which may be received through the network 108. Input device 102 may include voice recognition equipment and/or software that processes auditory inputs from the test subject. For example, the auditory input from the subject, in order to show recognition of the visual indicia, may be a verbalization of the trait possessed by the visual indicia. In one embodiment, if the trait is a direction orientation of a Landolt "C," the responsive auditory inputs may be "up," "down," "right," and "left." However, one skilled in the art will understand and appreciate that other auditory inputs may be used (e.g., stating a color, numeral, letter, symbol, etc.) to indicate that the subject perceived and/or recognized the visual indicia. It should be noted, however, that the present invention is not limited to implementation on such input devices 102, but may be implemented on any of a variety of different types of devices within the scope of embodiments hereof. Input indicating the subject's response to a displayed visual indicia may be received and captured with input device 102. If the trait is a directional orientation, a satisfactory test response may be identifying the direction that the visual indicia is facing. By way of example only, without limitation, identifying may include the subject providing input by manipulating a joystick in a direction corresponding to the directional orientation on a hand-held device employed as the input device 102.

If input device 102 is an eye tracking system, the position and/or focus of the eyes of subject may be monitored and an input registered when the eyes are positioned and/or focused at the proper location.

If input device 102 is a gesture recognition system, a variety of systems and/or methods may be used to receive inputs. For example, one or more cameras may be used to monitor the movement of a subject's body limbs and/or extremities and, in conjunction with appropriate hardware and/or software, register an input when subject makes an appropriate gesture. Gesture recognition systems may also utilize optical markers attached to subject to facilitate motion tracking. Transmitters attached to subject and receivers (for example, utilizing radio infrared, sonic, subsonic, or ultrasonic transmissions) may also be utilized as part of a gesture recognition system.

If input device 102 is a touch sensitive screen, any type of touch sensitive screen may be utilized. Also, an overlay of a touch sensitive material may be used to receive touch inputs in conjunction with a display that is not itself touch sensitive. Such an overlay may be any distance from the display.

The display device 120 may be capable of displaying output video visually observable by a subject and may be any type of computer, testing apparatus, or television monitor, including cathode ray tube, liquid crystal display, plasma screen, or any other display type, or may comprise a screen upon which images are projected, either from the front or from the rear. Further, the display device 120 may provide a user interface for a test administrator to interact with the test unit 110 before, during, and after administering the vision ability tests to a test subject.

The test unit 110, as shown in FIG. 1, may be any type of computing device, embodiments of which will be more fully discussed below with reference to FIGS. 4 and 5. The database 104 may be configured to store information associated with tests of visual ability. It will be understood and appreciated by those of ordinary skill in the art that the information stored in the database 104 may be configurable and may include any information relevant to the testing of visual ability. The content and volume of such information are not intended to limit the scope of embodiments of the present invention in any way. Although illustrated as a single, independent component, database 104 may, in fact, be a plurality of databases, for instance, a database cluster. Further, portions or the entirety of the database 104 may reside on a computing device associated with the test unit 110, another external computing device (not shown), and/or any combination thereof. One skilled in the art should appreciate that database 104 is optional and need not be implemented in conjunction with the computing system 100.

Returning to FIG. 1, the test unit 110 may include a presenting component 112, an input component 114, a testing component 116, and a processing component 118, shown in accordance with an embodiment of the present invention. It will be understood by those of ordinary skill in the art that the components 112, 114, 116, and 118 illustrated in FIG. 1 are exemplary in nature and in number, and should not be construed as limiting. Any number of components may be employed to achieve the desired functionality within the scope of embodiments of the present invention.

The presenting component 112 may be capable of displaying output video visually observable by a subject and may be any type of computer, testing apparatus, or television monitor, including cathode ray tube, liquid crystal display, plasma screen, or any other display type, or may comprise a screen upon which images are projected, either from the front or from the rear.

In one embodiment, presenting component 112 may be an apparatus that uses mirror and/or lenses strategically placed to generate a visual perspective of distance within a limited spatial area (e.g., providing a periphery configuration of mirrors to produce a tunnel effect). An example of such an apparatus is a perspective testing apparatus utilizing mirrors to generate a perspective of distance. Such an apparatus may include a mirror that displays the visual indicia in a central foveal area (i.e., directly in front of the subject), and may further include side mirrors that display a visual indicia to test peripheral visual ability.

In another embodiment, an apparatus may include lenses that change perceived distance and/or size of the displayed visual indicia to achieve a simulated distance. As a result, such an apparatus may provide a displayed visual indicia that appears to the test subject to be nearer or farther than the actual display. Thus, this configuration creates the perspective of optical infinity to the test subject.

One skilled in the art will appreciate that presenting component 112 may comprise multiple devices that, in combination, display some of the visual stimuli typical for a particular activity. In one embodiment, a single device may be used to display multiple displays of visual indicia (e.g., split-screen).

Presenting component 112 may alternatively comprise display glasses, goggles, visors, and the like, that may be worn by a subject to provide a visual display for the subject that is not typically visible to others. Additionally, presenting component 112 may provide a two dimensional or three dimensional image to the test subject. The three dimensional image display may include virtual reality or holographic presentations to the subject.

In operation, the presenting component 112 may be configured to present one or more visual indicia to a test subject. As discussed more fully below, presenting component 112 may present visual indicia in varying ways to test different aspects of the subject's visual ability. In general, each of the visual indicia may possess a trait or traits. This trait may be, for example, a directional orientation (e.g., arrow, Landolt "C", Tumbling E, etc.), a position on a user interface (e.g., located in a particular quadrant of the display), one of a predetermined number of mutually exclusive traits (e.g., indicator that faces either up, down, left, or right), or any combination of traits. Further, one of ordinary skill in the art will understand and appreciate that other traits may be used, and the present invention is not limited to any particular trait.

The input component 114 may be configured to receive input from the test subject (e.g., by utilizing input device 102). Any suitable receiving component that is capable of receiving input provided by the subject may be used in accordance with this invention. By way of example, without limitation, the subject may provide input utilizing a keyboard, joystick, trackball, or the like. The input may depend upon the presenting component. For example, if the presenting component is touch-sensitive, the subject could provide input by touching the presenting component. In another embodiment, the input component could have voice recognition capability, where the subject may provide input with a vocalized response that is recognized by the input component. One skilled in the art will understand and appreciate that any suitable input component may be used in accordance with the present invention. Certain types may be preferred based on the tests presented by the presenting component and, as discussed above, the capabilities of the presenting component. After receiving input from the subject, the input component 114 may store the input, for instance, in database 104 for future reference.

The testing component 116 is configured to provide tests to the subject. As will be discussed more fully below with respect to FIG. 2, testing component 116 may provide two or more tests to determine the visual ability of a subject. More specifically, multiple tests may be provided at a unitary location, such as test unit 110. Further, testing component 116 is configurable so that the tests may vary depending on the subject. For example, the tests may vary given the test subject's particularized sport or activity, competition level, visual strengths/weaknesses, etc. Thus, the testing component 116 may also be responsible for determining the tests (and level or difficulty of tests) presented by the presenting component 112.

Figure 3:
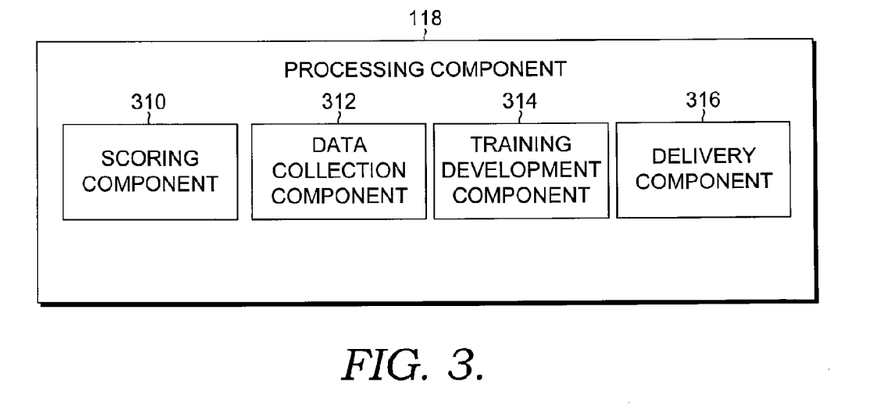
FIG. 3 illustrates a block diagram of an exemplary processing component for use in implement the present invention.

The processing component 118 is provided to process the input received by input component 114. As shown in FIG. 3, the processing component 118 may comprise a scoring component 310, a data collection component 312, a training development component 314, and a delivery component 316. The scoring component 310 may be configured to utilize a scoring algorithm to derive a score based on the subject's response to the tests presented. The subject's responses may be determined by comparing such response to those from a particular population, typically retrieved from the database 104. The scoring component 310 may provide an evaluation of the visual ability of the subject incident to receiving and measuring one or more responses to the visual indicia. Once a score (e.g., percentile) is determined, it may be presented to the subject via presenting component 112. The score may be presented at the conclusion of each test, at the conclusion of all tests, or a combination thereof.

The data collection component 312 is configured to collect the data received from input component 114. Such data may then be stored, for example, in database 104. The data collected may further be used to create standards for a particular population, which may then be used by scoring component 310. One of skill in the art will appreciate that database 104 and/or scoring component 310 may be located remotely from other components of system 100.

The training development component 314 is configured to develop a training plan or regimen for the test subject based on the collected data and determined scores. In embodiments of the present invention, test unit 110 may be used for training the test subject, after the subject has undergone testing.

The delivery component 316 is configured to transmit the determined score, collected data, and the like to presenting component 112. The delivery component 316 may additionally provide this data to an external computing device, such as central location 106, for further consideration, analysis, or storage. In one embodiment, the delivery component 316 may provide data in real time to testing component 116, such that the tests may be configured or varied while still in the testing process. It should be understood and appreciated by those of ordinary skill in the art that, although embodiments and examples are discussed above, the delivery component 316 may provide information related to testing visual ability to any component of the computing system 100, both internal and external to the test unit 110.

One skilled in the art will appreciate that the delivery component 316 may send information from test unit 110 at any desired frequency. That is, the information may be sent to a desired location, for example, after a subject completes all tests or, alternatively, after each individual test. If sending the information to central location 106 or database 104 for storage and/or processing, the information may be sent collectively for all subjects at the end of the day. The frequency may depend upon the storage capacity and processing capability of the test unit 110, as well as the desired use of the information.

Figure 2:
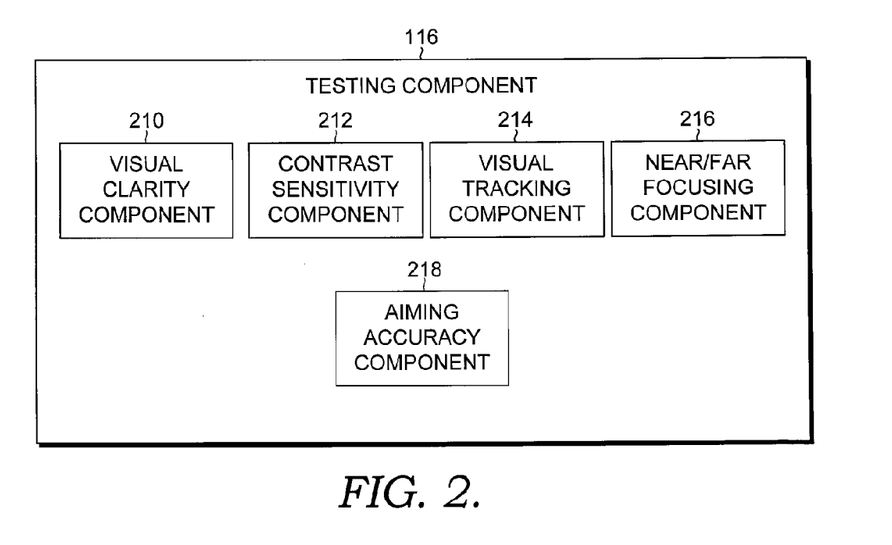
FIG. 2 illustrates a block diagram of an exemplary testing component for use in accordance with an embodiment of the present invention.

Referring now to FIG. 2, testing component 116 is further illustrated. Testing component 116 may comprise a visual clarity component 210, a contrast sensitivity component 212, a visual tracking component 214, a near/far focusing component 216, and a fixation disparity component 218. Additional components may comprise target acquisition, visual acuity, dynamic visual acuity, gaze stability, depth perception, binocular vision, or any other visual skill. Each of these components may be used by test unit 110 to test various aspects of an individual's visual ability. One skilled in the art will appreciate that other visual tests may be used and are within the scope of the invention, and that any combination of these and/or other test components may be utilized.

The visual clarity component 210 is configured to test the visual clarity of a subject, and may include displaying a visual indicia at a certain predetermined distance and requiring the subject to identify the indicia. For example, the visual indicia may be presented in a smaller size until the subject can no longer identify the indicia. A typical eyechart may be used for such a test. Alternatively, a Landolt "C" may be presented to the subject. In one embodiment, the visual indicia may be presented using a testing apparatus as the presenting component 112 to simulate the distance from the subject to the visual indicia. One skilled in the art will appreciate and understand that any suitable test that tests a subject's visual clarity may be used by the visual clarity component 210.

The contrast sensitivity component 212 is configured to test the contrast sensitivity of the test subject. Such a test may be used to measure a subject's ability to perceive different luminosities in a static image. In one embodiment, a visual indicia having two different luminosities is presented to a subject. The subject may then be required to identify a characteristic of the visual indicia that requires the subject to discern the different luminosities presented. One skilled in the art will appreciate and understand that any suitable test of contrast sensitivity may be used by the contrast sensitivity component 212.

The visual tracking component 214 is configured to test the visual tracking capabilities of a test subject. Any suitable test may be used and is within the scope of this invention. By way of example, without limitation, a visual indicia, such as a box, may be presented to the test subject. The box may then move in various directions on the display device at various speeds. The subject then must identify a second visual indicia, such as a Landolt "C", that may be presented inside of the box. Such a test requires the subject to track the first visual indicia before identifying the second visual indicia, thereby testing the subject's visual tracking ability.

The near/far focusing component 216 is configured to test the ability of a subject in changing their visual focus from near to far and far to near. By way of example, without limitation, this component may utilize two or more display devices for presenting component 112, where a far display device is located at or near optical infinity from a subject and a near display device is located at differing distances from the subject. The subject may then be required to identify visual indicia displayed on both display devices, which tests the subject's ability to focus at varying distances.

The visual aiming component 218 is configured to test the ability of a subject in visually aiming an object. By way of example, without limitation, this component may utilize two aligning bars or other indicia above and below a target object. The subject then may work, using an input device, to align each of the two bars to be aligned with the target object. This may work to test the eye pointing accuracy and stability of the subject. Of course, more than two or fewer than two bars or other indicia may be used. This invention, however, contemplates any method of testing the visual aiming of a subject. Similarly, the depth perception of a subject may be tested by having subject align bar(s) or other indicia with a target object.

Figure 4:
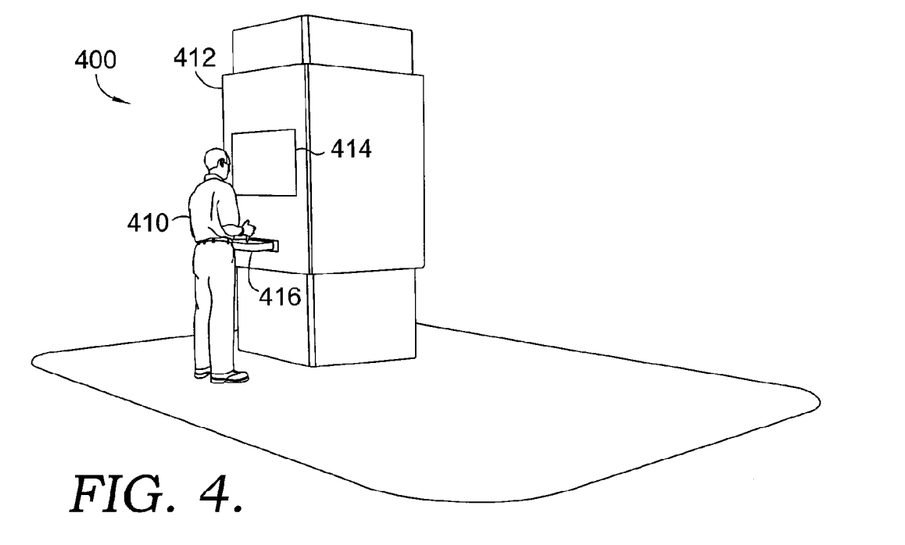
FIG. 4 illustrates an exemplary unitary visual testing unit, in accordance with an embodiment of the present invention.

Referring now to FIG. 4, an exemplary visual testing system 400 is illustrated, in accordance with an embodiment of the present invention. A subject 410 participating in testing may use visual testing system 400 to test the visual ability of subject 410 during an activity. Test unit 412 comprises a display device 414 and an input device 416. In this embodiment, the testing unit 412 may receive inputs from subject 410 via input device 416 that is connected (e.g., by a wired or wireless connection) to test unit 412. One skilled in the art will appreciate that subject 410 may provide input to test unit 412 via any type of input device and that subject 412 may interact with input device 416 through any means (e.g., physical interaction, voice recognition) in order to provide the appropriate response.

By having a unitary test unit, such as test unit 412, that is capable of presenting several tests to a subject, an overall evaluation of the subject's visual ability may be provided. Further, because test unit 412 may include processing capabilities, it is able to process the data, resulting in a determined score and/or a training regimen for the subject.

Figure 5:
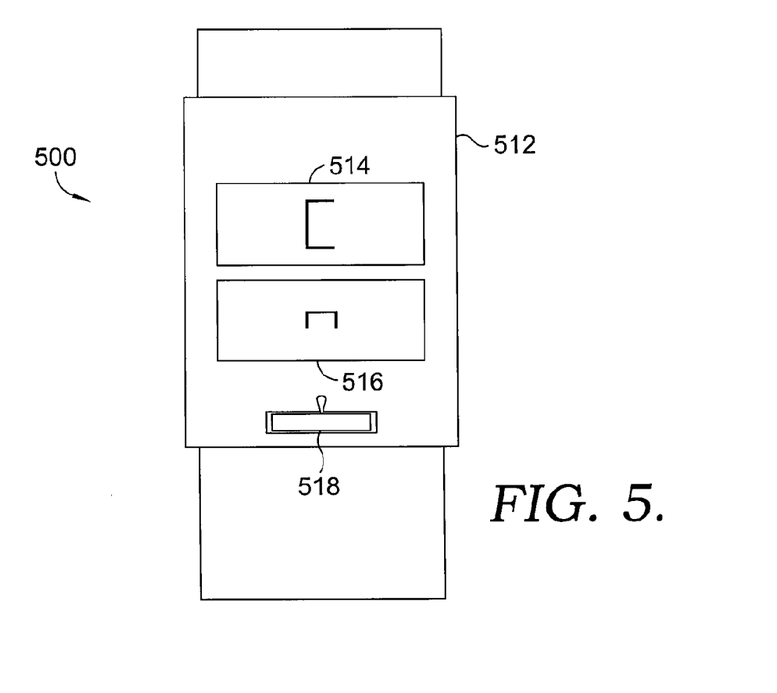
FIG. 5 illustrates another embodiment of a unitary visual testing unit, in accordance with the present invention.

FIG. 5 illustrates a visual testing system 500, in accordance with an embodiment of the present invention. In this embodiment, the vision tests are presented using two display devices 518 and 520. Having two display devices allows both devices to be used in presenting visual indicia to the subject. As discussed above, certain visual tests (e.g., near/far focusing) may work better if using multiple display devices. The input device 516 shown in FIG. 5 is illustrated as a joystick; however, any type of input device is contemplated to be within the scope of this invention.

Figure 6:
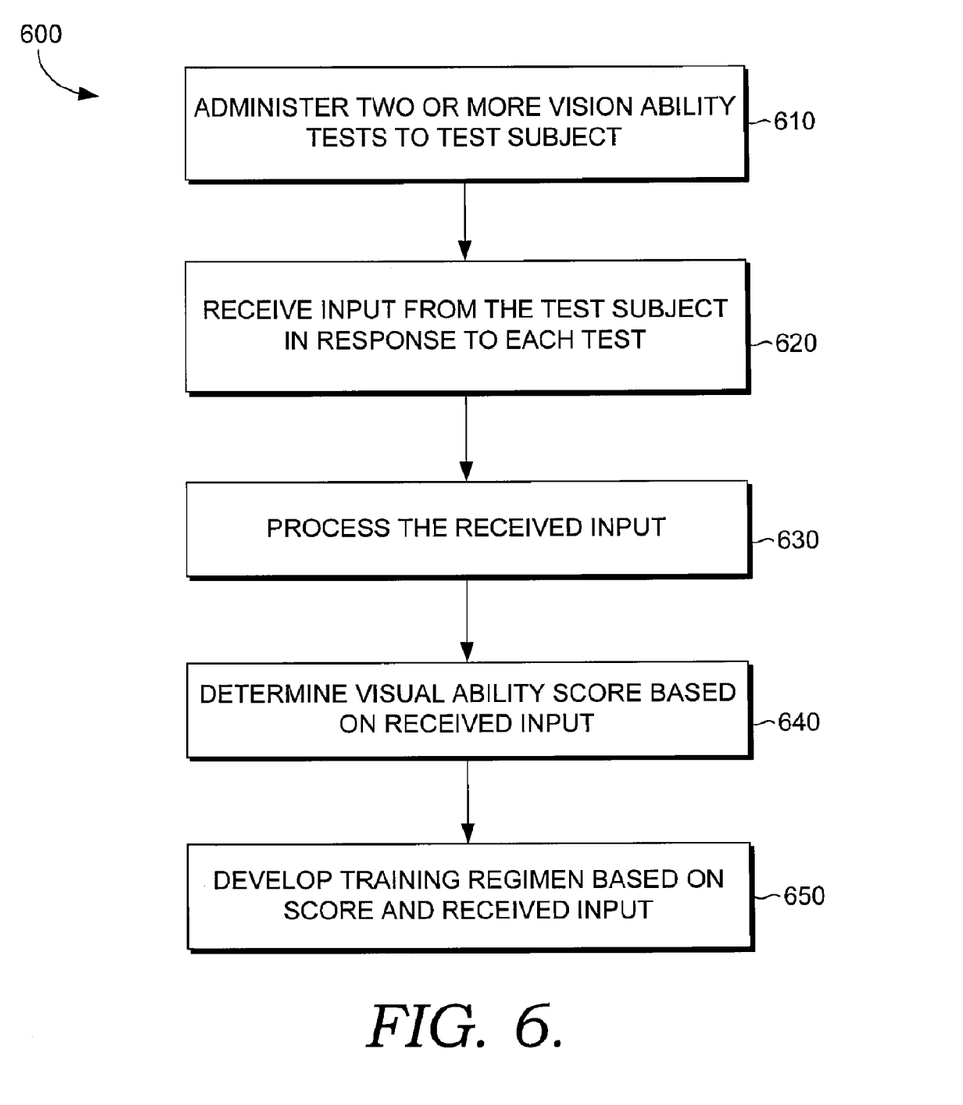
FIG. 6 illustrates a flow diagram showing a method for testing the visual ability of a subject at a unitary location, in accordance with an embodiment of the present invention.

Referring to FIG. 6, a flow diagram 600 is illustrated that shows a method of testing the visual abilities of a subject. Although the terms "step" and "block" are used hereinbelow to connote different elements of methods employed, the terms should not be interpreted as implying any particular order among or between various steps herein disclosed unless and except when the order of individual steps is explicitly described. Initially, two or more vision ability tests are administered to a test subject (e.g., utilizing test unit 110 of FIG. 1). This is shown at block 610. One skilled in the art will appreciate that any of the vision ability tests described above may be administered, as well as any other test that measures an individual's visual ability. Although each of the visual tests administered by the test unit may occur in any order, a visual clarity test is typically administered to a subject first in order to provide baseline information on the subject's vision. While the test is administered to the subject, the subject may provide the appropriate response by interacting with an input device that is connected to the test unit via an input component. This is indicated at block 620. A processing component (e.g., processing component 118 in FIG. 1) may then process the received input by, for example, collecting the data, determining a score, etc. The data may be stored, for example, in database 104, or sent via a delivery component to, for example, central location 106. This is indicated at block 630.

Optionally, at block 640, the data received from the subject's input with each test may be used to determine a score for the subject. An individual score may be determined for each test, and an overall score may be determined based on the data from all tests. The score may further be based on corresponding data for a particular population, and the subject's score may be compared accordingly (e.g., the subject may be given a percentile of their performance). At block 650, a training regimen may be developed for the test subject to train his or her visual ability based on, for example, their determined score and their received input in response to the vision ability tests.

The present invention has been described in relation to particular embodiments, which are intended in all respects to be illustrative rather than restrictive. Alternative embodiments will become apparent to those of ordinary skill in the art to which the present invention pertains without departing from its scope.

From the foregoing, it will be seen that this invention is one well adapted to attain all the ends and objects set forth above, together with other advantages which are obvious and inherent to the system and method. It will be understood that certain features and sub-combinations are of utility and may be employed without reference to other features and sub-combinations. This is contemplated by and is within the scope of the claims.

What is claimed is:

1. A device for testing the visual ability of a subject comprising:

a presenting component configured to present two or more vision ability tests, wherein the subject provides input in response to each test;

an input component configured to receive the input provided by the subject;

a processing component configured to process the received input; and a training development component configured to provide a visual ability training regimen for the subject.

2. The device of claim 1, wherein the processing component comprises a scoring component that determines a score based on the received input.

3. The device of claim 2, wherein the training development component provides the training regimen based on the determined score.

4. The device of claim 1, wherein one of the two or more vision ability tests includes a visual clarity test.

5. The device of claim 4, wherein the visual clarity test comprises a visual indicia presented at a specified size to the subject, and wherein the size increases until the visual indicia is identified by the subject.

6. The device of claim 5, wherein the visual indicia is a Landolt C.

7. The device of claim 1, wherein one of the two or more vision ability tests includes a contrast sensitivity test.

8. The device of claim 7, wherein the contrast sensitivity test comprises at least one visual indicia with one or more specified luminosities presented to the subject.

9. The device of claim 1, wherein one of the two or more vision ability tests includes a distance focusing test.

10. The device of claim 9, wherein distance focusing test comprises presenting a first visual indicia at a distance close to the subject and presenting a second visual indicia at a distance far from the subject.

11. A method of testing the visual ability of a test subject, wherein the method occurs at a unitary location, the method comprising:

administering two or more vision ability tests to a test subject; receiving input from the test subject in response to each test;

processing the received input; and providing a visual ability training regimen, based in part, on the received input.

12. The method of claim 11, wherein the method further comprises determining a score based on the received input.

13. The method of claim 12, wherein providing the visual ability training regimen is based, at least in part, on the determined score.

14. The method of claim 11, wherein one of the two or more vision ability tests includes a visual clarity test.

15. The method of claim 14, wherein the visual clarity test comprises a visual indicia presented at a specified size to the subject, and wherein the size increases until the visual indicia is identified by the subject.

16. The method of claim 15, wherein the visual indicia is a Landolt C.

17. The method of claim 11, wherein one of the two or more vision ability tests includes a contrast sensitivity test.

18. The method of claim 17, wherein the contrast sensitivity test comprises at least one visual indicia with one or more specified luminosities presented to the subject.

19. The method of claim 11, wherein one of the two or more vision ability tests includes a distance focusing test.

20. The method of claim 19, wherein distance focusing test comprises presenting a first visual indicia at a distance close to the subject and presenting a second visual indicia at a distance far from the subject.

21. A device for testing the visual ability of a subject comprising:

a presenting component configured to present two or more vision ability tests, wherein one of the two or more vision ability tests includes a distance focusing test, and wherein the subject provides input in response to each test;

an input component configured to receive the input provided by the subject;

a processing component configured to process the received input;

a scoring component that determines a score based on the received input; and a training development component that provides a visual ability training regimen for the subject, based in part, on a determined score.

* * * * *